US010912429B2

(12) United States Patent
Moriwaki

(10) Patent No.: US 10,912,429 B2
(45) Date of Patent: Feb. 9, 2021

(54) TOILET PAPER

(71) Applicant: DAIO PAPER CORPORATION, Shikokuchuo (JP)

(72) Inventor: Teppei Moriwaki, Fujinomiya (JP)

(73) Assignee: DAIO PAPER CORPORATION, Ehime (JP)

( * ) Notice: Subject to any disclaimer, the term of this patent is extended or adjusted under 35 U.S.C. 154(b) by 152 days.

(21) Appl. No.: 16/090,225

(22) PCT Filed: Feb. 27, 2017

(86) PCT No.: PCT/JP2017/007307
§ 371 (c)(1),
(2) Date: Sep. 29, 2018

(87) PCT Pub. No.: WO2017/169414
PCT Pub. Date: Oct. 5, 2017

(65) Prior Publication Data
US 2019/0110648 A1 Apr. 18, 2019

(30) Foreign Application Priority Data

Mar. 31, 2016 (JP) ................................. 2016-070122

(51) Int. Cl.
*A47K 10/16* (2006.01)
*A61L 9/01* (2006.01)

(52) U.S. Cl.
CPC ................ *A47K 10/16* (2013.01); *A61L 9/01* (2013.01)

(58) Field of Classification Search
CPC .................................... A47K 10/16; A61L 9/01
See application file for complete search history.

(56) References Cited

U.S. PATENT DOCUMENTS

| 2,639,939 | A | * | 5/1953 | Matchett | A47K 10/32 242/599.3 |
| 6,425,530 | B1 | * | 7/2002 | Coakley | A61L 9/04 239/52 |
| 9,708,569 | B2 | * | 7/2017 | Nakano | C11B 9/003 |
| 10,517,978 | B2 | * | 12/2019 | Miyamura | D06M 11/83 |

(Continued)

FOREIGN PATENT DOCUMENTS

| JP | 55077493 U | 5/1980 |
| JP | 05027106 Y2 | 7/1993 |

(Continued)

OTHER PUBLICATIONS

International Preliminary Report on Patentability (IPRP) and Written Opinion dated Oct. 2, 2018 issued in International Application PCT/JP2017/007307.

(Continued)

*Primary Examiner* — William A. Rivera
(74) *Attorney, Agent, or Firm* — Holtz, Holtz & Volek PC

(57) ABSTRACT

Toilet paper includes a cylindrical paper tube, and belt-shaped paper wound around the paper tube as a core. Floral-note or fruity-floral-note fragrance is applied to the paper tube. The fragrance is a modification fragrance which, in a toilet space, modifies a fecal odor containing at least methyl mercaptan and hydrogen sulfide. An application amount of the modification fragrance is at least 0.4 mass % but no more than 6 mass % to the paper tube of the toilet paper.

12 Claims, 1 Drawing Sheet

(56) References Cited

U.S. PATENT DOCUMENTS

| | | | |
|---|---|---|---|
| 10,583,029 B2* | 3/2020 | Chang | A61L 28/0015 |
| 2005/0001051 A1* | 1/2005 | Dobler | A61L 9/042 |
| | | | 239/34 |
| 2015/0272403 A1* | 10/2015 | Silverman | A47K 10/16 |
| | | | 15/104.93 |
| 2015/0320267 A1* | 11/2015 | Pour | A47K 10/46 |
| | | | 242/398 |
| 2018/0071423 A1* | 3/2018 | Miyamura | D06M 13/288 |
| 2020/0040529 A1* | 2/2020 | Rouse | D21H 17/06 |

FOREIGN PATENT DOCUMENTS

| | | |
|---|---|---|
| JP | 06086687 U | 12/1994 |
| JP | 2000093344 A | 4/2000 |
| WO | 2013018805 A1 | 2/2013 |

OTHER PUBLICATIONS

"International Search Report (ISR) dated May 16, 2017 issued in International Application No. PCT/JP2017/007307".

"Japanese Decision to Dismiss the Amendment dated Nov. 14, 2017 issued in counterpart Japanese Application No. 2016-070122".

"Japanese Office Action dated Jul. 25, 2017 issued in counterpart Japanese Application No. 2016-070122".

"Japanese Office Action dated Nov. 14, 2017 issued in counterpart Japanese Application No. 2016-070122".

"Japanese Office Action dated Sep. 12, 2017 issued in counterpart Japanese Application No. 2016-070122".

"Written Opinion dated May 16, 2017 issued in International Application No. PCT/JP2017/007307".

Extended European Search Report (EESR) dated Oct. 9, 2019 issued in counterpart European Application No. 17773959.6.

Chinese Office Action (and English language translation thereof) dated Jul. 3, 2020 issued in Chinese Application No. 201780021051.4.

* cited by examiner

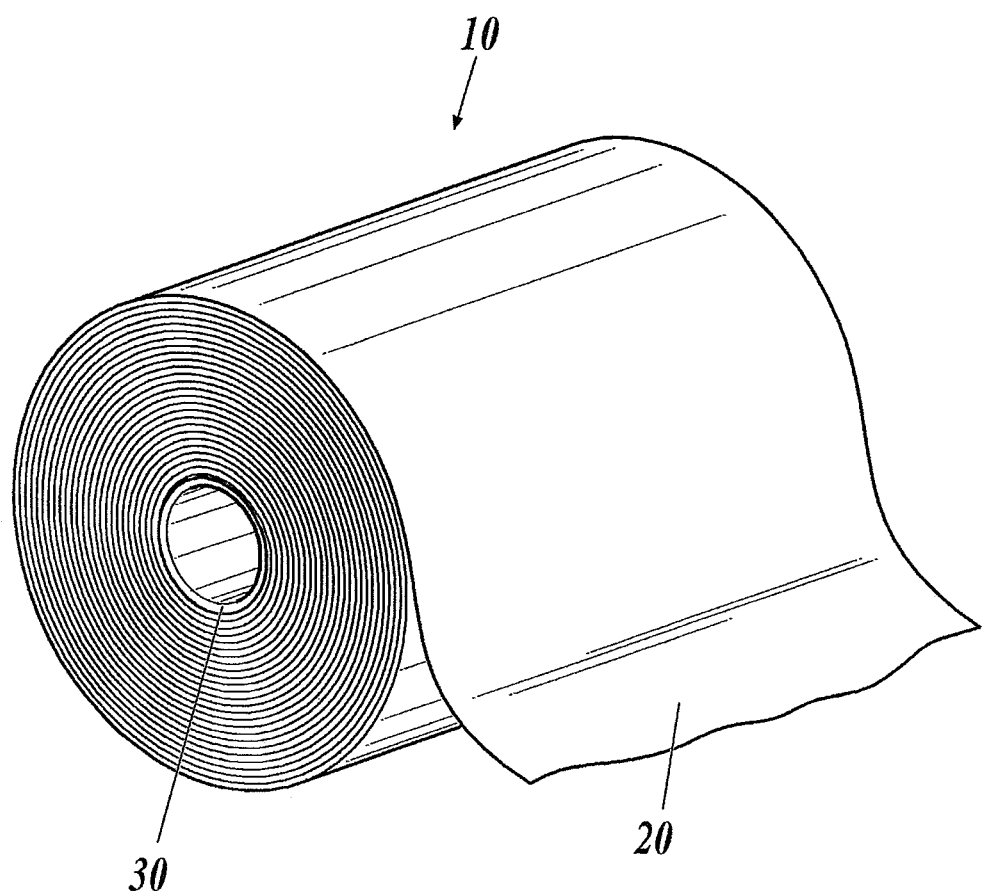

TOILET PAPER

TECHNICAL FIELD

The present invention relates to scented toilet paper.

BACKGROUND ART

There has been known toilet paper to reduce odors generated in a toilet space, the toilet paper always being ready in toilets and having a paper tube to which a fragrance is applied. (refer to, for example, Patent Document 1.)

RELATED ART DOCUMENTS

Patent Documents

Patent Document 1: Patent Application Publication No. 2000-93344

SUMMARY OF THE INVENTION

Problems to be Solved by the Invention

However, there is a limit on the applicable amount of the fragrance to the paper tube of the toilet paper of Patent Document 1.

In addition, among malodor components in toilets, in particular, a fecal odor is a complex odor composed of methyl mercaptan, hydrogen sulfide and so forth. Hence, it has been difficult to mask and deodorize the fecal odor with the fragrance emitted by the toilet paper.

Objects of the present invention include providing toilet paper which can more properly suppress the fecal odor.

Means for Solving the Problems

In order to solve the above problems, the present invention described in claim 1 is toilet paper including:

a cylindrical paper tube; and belt-shaped paper wound around the paper tube as a core, wherein a floral-note or fruity-floral-note fragrance is applied to the paper tube, and the fragrance is a modification fragrance which, in a toilet space, modifies a fecal odor containing at least methyl mercaptan and hydrogen sulfide, and an application amount of the modification fragrance is at least 0.4 mass % but no more than 6 mass % to the paper tube of the toilet paper.

Advantageous Effects of the Invention

According to the present invention, toilet paper which can more properly suppress the fecal odor is obtained.

BRIEF DESCRIPTION OF THE DRAWINGS

FIG. 1 is a perspective view showing toilet paper according to an embodiment(s).

EMBODIMENTS FOR CARRYING OUT THE INVENTION

Hereinafter, specific embodiments of toilet paper of the present invention are described in detail with reference to the drawing. However, the scope of the present invention is not limited to the illustrated example(s).

Toilet paper 10 includes, as shown in FIG. 1, a hollow cylindrical paper tube 30 and belt-shaped paper 20 wounded around the paper tube 30 as the core, for example.

The toilet paper 10 is usually used as follows: the toilet paper 10 is put on a paper holder, and the belt-shaped paper 20 is pulled.

Although size of the toilet paper 10 is not particularly limited, one having a diameter of 90 to 120 mm, a width of 100 to 120 mm and a paper tube diameter of 35 to 50 mm is common, and this is suitable for the present invention too.

Base paper constituting the belt-shaped paper 20 can be manufactured from a raw material for making thin paper containing raw material pulp as the main raw material. The raw material pulp is not particularly limited, and hence appropriate raw material pulp(s) can be used by being selected or mixed according to specific uses of the belt-shaped paper 20.

The number of plies and the basis weight of the belt-shaped paper 20 can be appropriately adjusted according to its use, but it is desired to use the belt-shaped paper 20 having the number of plies of 1 to 3 plies, a whole paper thickness of 90 to 270 µm, and a basis weight per ply of 10 to 30 g/m$^2$. The basis weight of less than 10 g/m$^2$ is preferable in terms of increase in softness, but it is difficult to properly ensure strength enough to be used. Meanwhile, if the basis weight is more than 30 g/m$^2$, the paper is hard as a whole, and also rough and accordingly harsh to the touch. Examples of the method for measuring the basis weight include a method inconformity to JIS P8124:2011.

The paper tube 30 is formed, for example, as a spiral paper tube made of paper-tube base paper being a spiral wound or a parallel wound paper tube.

The paper tube 30 is formed of, for example, two base paper layers of an inner-side base paper layer constituting the inner circumferential surface of the paper tube 30 and an outer-side base paper layer constituting the outer circumferential surface of the paper tube 30.

As the paper-tube base paper constituting each of the inner-side base paper layer and the outer-side base paper layer, base paper having a basis weight of 130 to 200 g/m$^2$ and a stiffness of 300 to 600 is preferably used in order to maintain strength. Examples of the method for measuring the stiffness include a method in conformity to JIS P8143:2009. By having the above stiffness, the paper-tube base paper can keep properness to form paper tubes, and also can maintain necessary strength as paper tubes of toilet paper. In addition, Cobb sizing degree (JIS P8140:1998) of the paper-tube base paper is preferably 35 to 70 so that the paper-tube base paper can obtain appropriate impregnation characteristics to impregnate fragrances.

The inner-side base paper layer and the outer-side base paper layer are joined with one another through an adhesive or the like as needed. Examples of the adhesive include: carboxymethyl cellulose; vinyl acetate; vinyl chloride; and polyvinyl alcohol. The application amount of the adhesive is not particularly limited, but 1 to 25 g/m$^2$ is appropriate. The above application amount of the adhesive can produce paper tubes having strength which is neither too high nor too low as paper tubes.

In particular, in the paper tube 30 of this embodiment, a modification fragrance is applied to at least one of the inner-side base paper layer and the outer-side base paper layer. In particular, in order to keep an aroma for a long period of time, it is desired that the fragrance is applied to the outer-side base paper layer which faces the belt-shaped paper when the belt-shaped paper 20 is wound around the paper tube 30, so that fresh air and the fragrance are less likely to directly contact one another, which is effective in maintaining an aroma.

The modification fragrance applied to the paper tube 30 is a modification fragrance which can modify the fecal odor. This modification fragrance modifies the odor containing at least methyl mercaptan and hydrogen sulfide.

The application amount of the modification fragrance applied to the paper tube 30 is at least 0.4 mass % but no more than 6 mass % to the mass of the paper tube 30. If the application amount is more than 6 mass % or mom, the strength decreases because of fragrance leakage from the paper-tube base paper, and accordingly necessary strength as paper tubes of toilet paper may not be maintained.

The modification fragrance is a fragrance which becomes a more pleasant smell when an unpleasant smell component (s), which is generally known as a malodor(s), is added. That is, the modification fragrance has an effect (called matching effect or harmonizing effect) of suppressing a malodor(s) by modifying into a more pleasant smell with an unpleasant smell component(s) being added to the modification fragrance, which itself has a pleasant smell. It is known that there are, among components obtained from plant-derived essential oils or the like, some components which can suppress malodors sensorily (e.g. Ando, 1991, Environmental Technology, Vol. 20, No. 5, 334-339).

In this embodiment, the modification fragrance itself contains a floral-note or fruity-floral-note fragrance, and preferably contains one of a rose note, a jasmine note, a green note, a lily note, and a citrus note, such as lemons or oranges, as a modification component.

The modification fragrance in this embodiment is a fragrance which modifies the fecal odor in toilets, to be specific, a fragrance which modifies the odor containing, among components constituting the fecal odor, 10 to 30 ppm of hydrogen sulfide and 0.5 to 2 ppm of methyl mercaptan, and gives the actual feeling of deodorization.

Examples of the jasmine-note fragrance can include the following ones: α-hexylcinnamic aldehyde; methyl dihydrojasmonate; methyl jasmonate; cis-jasmone; hydrocinnamaldehyde; benzyl formate; benzyl acetate; benzyl benzoate; jasminealdehyde; and benzyl propionate. These can be used alone, or two or more in combination.

Examples of the rose-note fragrance can include the following ones: β-phenylethyl alcohol; citronellol; nerol; geraniol; rose oxide; tetrahydrogeraniol; phenoxanol; 1-(2, 6,6-trimethyl-1-cyclohexenyl)-2-buten-1-one (β-damascone); β-phenylethyl phenylacetate; decyl acetate; geranyl benzoate; 2-phenylethyl acetate; citronellyl acetate; geranyl acetate; neryl acetate; geranyl propionate; formic acid β-phenylethyl; geranyl formate; citronellyl formate; isobutyl phenylacetate; benzophenone; geranyl butyrate; n-nonylalcohol; geranium oil; and rose oil. These can be used alone, or two or more in combination.

Examples of the green-note fragrance can include the following ones: cis-3-hexenylacetate; cis-3-hexenol; dimethyltetrahydrobenzaldehyde; p-ethyl-2,2-dimethylhydrocinamaldehyde; ethyl benzoate; bornyl acetate; farnesol; d-α-pinene, 3,3-dimethyl-5-(2,2,3-trimethyl-3-cyclopenten-1-yl)-4-penten-2-ol; 2-methyl-4-(2,2,3-trimethyl-3-cyclopenten-1-yl)-2-buten-1-ol; linalyl acetate; 1-octen-3-ol; phenylethyl alcohol; methyl anthranilate; and geraniol. These can be used alone, or two or more in combination.

Examples of the lily-note fragrance can include the following ones: linalool; linalyl acetate; ethyl linalool; p-cresol; α-terpineol; phenylethyl acetate; and phenylethyl cinnamate. These can be used alone, or two or more in combination.

Examples of the citrus-note fragrance can include the following ones: citral; isocyclocitral; dihydromyrcenol; bergamot oil; lemon oil; orange oil; limonene; octyl aldehyde; diphenylmethane; methylheptenone; geranial; dipentene; α-terpinene; neral; rhodinal (citrus note); terpinyl acetate; ethyl acetate; butyl butyrate; and sinensal. These can be used alone, or two or more in combination.

Next, results of performance evaluations of manufactured samples of examples and samples of comparative examples of toilet paper of the present invention are shown.

In this embodiment, there were manufactured: samples of the toilet paper 10 having the paper tube 30 which was manufactured by superposing two paper-tube base sheets spirally and to which a modification fragrance "TJP-O-4761" (Takasago International Corporation) was applied; and samples of toilet paper having the paper tube to which a conventionally used ordinary fragrance "Fruity Floral" (Ogawa & Co., Ltd.) was applied.

The application density of the fragrance was as shown in a Table. Further, the mass, diameter and width of the paper tube 30 were 4.7 g/tube, 41 mm and 114 mm, respectively. The basis weight and stiffness of the paper-tube base paper were 160 g/m$^2$ and 500, respectively.

(First Performance Evaluation)

The toilet paper 10 of each of the samples of the examples, the toilet paper 10 having the paper tube 30 to which the modification fragrance was applied, and the toilet paper of each of the samples of the comparative examples, the toilet paper having the paper tube to which the ordinary fragrance was applied, were used by 62 ordinary citizens in toilets at home, and they made a sensory evaluation about the fecal odor and evaluated the actual feeling of the deodorizing effect with a seven-point scale (felt it very much, felt it, somewhat felt it, neither, did not feel it much, did not feel it, did not feel it at all).

Then, the percentage of the people whose answer was "felt it very much" or "felt it" was calculated.

As a result, it was found that 63% of the testers felt the deodorizing effect of the sample of the example 1, whereas 44% of the testers felt the deodorizing effect of the sample of the comparative example 1. (Refer to Table 1.)

Hence, the toilet paper 10 having the paper tube 30 to which the modification fragrance is applied can properly suppress the fecal odor by being used in toilets.

(Second Performance Evaluation)

From the toilet paper 10 of each of the samples of the examples, the paper tube 30 was taken out, and from the paper tube 30, a 0.1 [g] specimen was cut out. Similarly, from the toilet paper of each of the samples of the comparative examples, the paper tube was taken out, and from the paper tube, a 0.1 [g] specimen was cut out.

As a reference simulative fecal odor were used odor components obtained from a subject under a normal health condition according to Sato et al. (Journal of Health Science, 2002). More specifically, they were 20 ppm of hydrogen sulfide, 1 ppm of methyl mercaptane, 6 ppm of acetic acid, 1 ppm of propionic acid, 0.2 ppm of isobutyric acid, 0.1 ppm of isovaleric acid, 0.2 ppm of valeric acid, and 7 ppm of pyridine.

The specimens of the samples of the examples and the specimens of the samples of the comparative examples were respectively sealed in 45 L polyester bags, and the bags were filled with odor-free air and left to stand one hour. Thereafter, the above odor components were generated in the 45

L polyester bags with an intensity corresponding to the odor intensity "3" in the six grades odor intensity measurement method, and change in the odor intensity was measured with the six grades odor intensity measurement method. The number of testers was 15. If the volume of a toilet space is 4 m³, a 0.1 g specimen put in a 45 L bag simulates a state in which two toilet rolls are placed in the toilet space. As to the evaluation, decrease in the odor intensity by one or more levels from "3" as the reference, namely, the odor intensity being 2.0 or lower, was regarded to be acceptable. The above test is based on the deodorant effectiveness testing method (sensory deodorization) by Air Fresheners & Deodorizers Conference.

Consequently, the odor intensity "0" was obtained from the specimen of the sample of the example 1 in the six grades odor intensity measurement method, whereas the odor intensity "2.2" was obtained from the specimen of the sample of the comparative example 1 in the six grades odor intensity measurement method.

The fragrance's application density was examined, and consequently it was determined that the application density of 0.4 mass % had the deodorizing effect as indicated by the example 2, whereas the application density of 0.2 mass % did not have the expected deodorizing effect. (Refer to Table 1.)

The strength necessary as paper tubes of toilet paper was examined. Samples in which the paper tube was deformed in the winding machine because of an excessive amount of the fragrance are indicated by "×" (cross), whereas samples in which the paper tube was not deformed are regarded to be acceptable and indicated by "○" (circle).

As a result, as indicated by the example 3, the application density of 5.3 mass % did not cause the paper tube deformation, whereas as indicated by the comparative example 3, the application density of 10.6 mass % caused the paper tube deformation. (Refer to Table 1.)

In the above embodiment, as the modification fragrance, the "TJP-O-4761" was used. This is not, however, intended to limit the present invention, and hence another modification fragrance may be used.

Further, it is a matter of course that, in addition to the above, specific detailed structures and so forth can also be appropriately modified.

INDUSTRIAL APPLICABILITY

The present invention can be properly utilized in the manufacturing field of toilet paper.

DESCRIPTION OF REFERENCE NUMERALS

10 Toilet Paper
20 Belt-shaped Paper
30 Paper Tube

The invention claimed is:

1. Toilet paper comprising:
a cylindrical paper tube; and
belt-shaped paper wound around the paper tube,
wherein:
a fragrance is applied to the paper tube,
the fragrance is a modification fragrance which modifies a fecal odor containing at least methyl mercaptan and hydrogen sulfide, and
an amount of the modification fragrance that is applied to the paper tube is at least 0.4 mass % but no more than 6 mass % with respect to a mass of the paper tube.

2. The toilet paper according to claim 1, wherein the modification fragrance is a floral-note or fruity-floral-note fragrance.

3. The toilet paper according to claim 1, wherein the amount of the modification fragrance that is applied to the

TABLE 1

| | Application amount g/paper tube | Application density % | Type of fragrance | Evaluation of actual use (First performance evaluation) % of people actually feeling effect | Evaluation of odor strength (Second performance evaluation) Evaluation of odor strength | Strength of paper tube |
|---|---|---|---|---|---|---|
| Example 1 | 0.12 | 2.6 | Modification fragrance | 63% | 0 | ○ |
| Example 2 | 0.02 | 0.4 | Modification fragrance | 55% | 1.7 | ○ |
| Example 3 | 0.25 | 5.3 | Modification fragrance | 78% | 0 | ○ |
| Comparative example 1 | 0.12 | 2.6 | Ordinary fragrance | 44% | 2.2 | ○ |
| Comparative example 2 | 0.01 | 0.2 | Modification fragrance | 40% | 2.2 | ○ |
| Comparative example 3 | 0.5 | 10.6 | Modification fragrance | 80% | 0 | X |

Hence, the toilet paper 10 having the paper tube 30 to which the modification fragrance having the harmonizing effect is applied can properly suppress the fecal odor by being used in toilets.

As described above, the toilet paper 10 having the paper tube 30 to which the modification fragrance which modifies the fecal odor is applied can more properly suppress the fecal odor than the conventional toilet paper having the paper tube to which the ordinary fragrance is applied.

paper tube is at least 2.6 mass % but no more than 6 mass % with respect to a mass of the paper tube.

4. The toilet paper according to claim 1, wherein the amount of the modification fragrance that is applied to the paper tube is at least 2.6 mass % but no more than 5.3 mass % with respect to a mass of the paper tube.

5. The toilet paper according to claim 1, wherein the paper tube comprises an inner-side paper layer and an outer-side paper layer that faces the belt-shaped paper.

6. The toilet paper according to claim 5, wherein the modification fragrance is applied to the outer-side paper layer that faces the belt-shaped paper.

7. The toilet paper according to claim 1, wherein the modification fragrance includes at least one of α-hexylcinnamic aldehyde, methyl dihydrojasmonate, methyl jasmonate, cis-jasmone, hydrocinnamaldehyde, benzyl formate, benzyl acetate, benzyl benzoate, jasminealdehyde, and benzyl propionate.

8. The toilet paper according to claim 1, wherein the modification fragrance includes at least one of ρ-phenylethyl alcohol, citronellol, nerol, geraniol, rose oxide, tetrahydrogeraniol, phenoxanol, 1-(2,6,6-trimethyl-1-cyclohexenyl)-2-buten-1-one (β-damascone), β-phenylethyl phenylacetate, decyl acetate, geranyl benzoate, 2-phenylethyl acetate, citronellyl acetate, geranyl acetate, neryl acetate, geranyl propionate, formic acid β-phenylethyl, geranyl formate, citronellyl formate, isobutyl phenylacetate, benzophenone, geranyl butyrate, n-nonylalcohol, geranium oil, and rose oil.

9. The toilet paper according to claim 1, wherein the modification fragrance includes at least one of cis-3-hexenylacetate, cis-3-hexenol, dimethyltetrahydrobenzaldehyde, p-ethyl-2,2-dimethylhydrocinamaldehyde, ethyl benzoate, bornyl acetate, farnesol, d-α-pinene, 3,3-dimethyl-5-(2,2,3-trimethyl-3-cyclopenten-1-yl)-4-penten-2-ol, 2-methyl-4-(2,2,3-trimethyl-3-cyclopenten-1-yl)-2-buten-1-ol, linalyl acetate, 1-octen-3-ol, phenylethyl alcohol, methyl anthranilate, and geraniol.

10. The toilet paper according to claim 1, wherein the modification fragrance includes at least one of linalool, linalyl acetate, ethyl linalool, p-cresol, α-terpineol, phenylethyl acetate, and phenylethyl cinnamate.

11. The toilet paper according to claim 1, wherein the modification fragrance includes at least one of citral, isocyclocitral, dihydromyrcenol, bergamot oil, lemon oil, orange oil, limonene, octyl aldehyde, diphenylmethane, methylheptenone, geranial, dipentene, α-terpinene, neral, rhodinal, terpinyl acetate, ethyl acetate, butyl butyrate, and sinensal.

12. The toilet paper according to claim 1, wherein a Cobb sizing degree (JIS P8140:1998) of a base paper of the paper tube is 35 to 70.

\* \* \* \* \*